(12) United States Patent
Jang

(10) Patent No.: US 6,821,287 B1
(45) Date of Patent: Nov. 23, 2004

(54) MULTI-MODE VASCULAR CATHETER SYSTEM

(75) Inventor: G. David Jang, Redlands, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1826 days.

(21) Appl. No.: 07/705,295

(22) Filed: May 24, 1991

(51) Int. Cl.[7] .............................................. A61M 29/02
(52) U.S. Cl. ...................................... 606/194; 604/160
(58) Field of Search .......................... 604/96–103, 160; 606/192–196

(56) References Cited

U.S. PATENT DOCUMENTS

| | | |
|---|---|---|
| 3,262,449 A | 7/1966 | Pannier et al. |
| 3,297,030 A | 1/1967 | Czorny et al. |
| 3,550,591 A | 12/1970 | MacGregor |
| 3,682,173 A | 8/1972 | Center |
| 3,853,130 A | 12/1974 | Sheridan |
| 4,037,599 A | 7/1977 | Raulerson |
| 4,054,136 A | 10/1977 | von Zeppelin |
| 4,079,738 A | 3/1978 | Dunn et al. |
| 4,147,165 A | 4/1979 | Tauschinski |
| 4,175,564 A | 11/1979 | Kwak |
| 4,323,071 A | 4/1982 | Simpson et al. |
| 4,411,055 A | 10/1983 | Simpson |
| 4,411,654 A | 10/1983 | Boarini et al. |
| 4,439,185 A | 3/1984 | Lundquist |
| 4,468,224 A | 8/1984 | Enzmann et al. |
| RE31,855 E | 3/1985 | Osborne |
| 4,516,972 A | 5/1985 | Samson |
| 4,538,622 A | 9/1985 | Samson et al. |
| 4,554,929 A | 11/1985 | Samson et al. |
| 4,569,347 A | 2/1986 | Frisbie |
| 4,573,470 A | 3/1986 | Samson et al. |
| 4,581,017 A | 4/1986 | Sahota |
| 4,582,181 A | 4/1986 | Samson |

(List continued on next page.)

FOREIGN PATENT DOCUMENTS

| | | |
|---|---|---|
| EP | 0274129 A2 | 7/1988 |
| EP | 0282143 A1 | 9/1988 |
| EP | 0388112 A2 | 9/1990 |
| EP | 0416662 B1 | 3/1991 |
| WO | WO 82/03558 | 10/1982 |
| WO | WO 91/05512 | 5/1991 |
| WO | WO 92/17236 | 10/1992 |

OTHER PUBLICATIONS

Suggested Directions for Use, Outside™ Ultra Low Profile Coronary Balloon Dilatation Catheter, Mansfield, Boston Scientific Corporation.

*Primary Examiner*—Cary E. O'Connor
(74) *Attorney, Agent, or Firm*—McAndrews, Held & Malloy, Ltd.

(57) ABSTRACT

An intravascular catheter, comprising a catheter shaft having a proximal end and a distal end, and a guidewire lumen extending through the shaft for receiving a steerable guidewire, wherein the guidewire lumen has a proximal opening at the proximal end of the shaft for insertion of a guidewire into the lumen, and a side port for insertion of a guidewire into the lumen through the side of the catheter shaft, the side port located distally of the proximal opening and inside the patient during use, the side port being adapted to direct guidewire to extend through the side port distally into the guidewire lumen while preventing a guidewire from extending through the side port proximally into the guidewire lumen. Also disclosed are methods for using the catheter.

14 Claims, 9 Drawing Sheets

U.S. PATENT DOCUMENTS

| | | | |
|---|---|---|---|
| 4,585,013 A | | 4/1986 | Harris |
| 4,596,559 A | | 6/1986 | Fleischhacker |
| 4,616,652 A | | 10/1986 | Simpson |
| 4,619,644 A | | 10/1986 | Scott |
| 4,631,056 A | | 12/1986 | Dye |
| 4,631,059 A | | 12/1986 | Wolvek et al. |
| 4,638,805 A | | 1/1987 | Powell |
| 4,705,507 A | * | 11/1987 | Boyles .................. 604/101 |
| 4,723,948 A | | 2/1988 | Clark et al. |
| 4,738,666 A | * | 4/1988 | Fuqua ................... 604/280 |
| 4,747,833 A | | 5/1988 | Kousai et al. |
| 4,748,982 A | * | 6/1988 | Horzewski et al. ......... 606/192 |
| 4,748,986 A | | 6/1988 | Morrison et al. |
| 4,762,129 A | | 8/1988 | Bonzel |
| 4,771,777 A | | 9/1988 | Horzewski et al. |
| 4,813,930 A | | 3/1989 | Elliott |
| 4,821,722 A | | 4/1989 | Miller et al. |
| 4,865,593 A | | 9/1989 | Ogawa et al. |
| 4,883,468 A | | 11/1989 | Kousai et al. |
| 4,888,000 A | | 12/1989 | McQuilkin et al. |
| 4,898,577 A | | 2/1990 | Badger et al. |
| 4,931,049 A | | 6/1990 | Klimas |
| 4,944,745 A | * | 7/1990 | Sogard et al. ............... 606/194 |
| 4,947,864 A | | 8/1990 | Shockey et al. |
| 4,981,478 A | | 1/1991 | Evard et al. |
| 4,988,356 A | * | 1/1991 | Crittendon et al. ......... 606/192 |
| 4,997,424 A | | 3/1991 | Little |
| 5,024,234 A | | 6/1991 | Leary et al. |
| 5,034,001 A | | 7/1991 | Garrison et al. |
| 5,046,503 A | * | 9/1991 | Schneiderman ............. 128/692 |
| 5,061,267 A | * | 10/1991 | Zeiher ......................... 606/40 |
| 5,061,273 A | * | 10/1991 | Yock .......................... 606/194 |
| 5,102,403 A | | 4/1992 | Alt |
| 5,135,482 A | | 8/1992 | Neracher |
| 5,135,535 A | | 8/1992 | Kramer |
| 5,154,725 A | | 10/1992 | Leopold |
| 5,171,222 A | | 12/1992 | Euteneuer et al. |
| 5,195,978 A | | 3/1993 | Schiffer |
| 5,205,822 A | | 4/1993 | Johnson et al. |
| 5,267,982 A | | 12/1993 | Sylvanowicz |

* cited by examiner

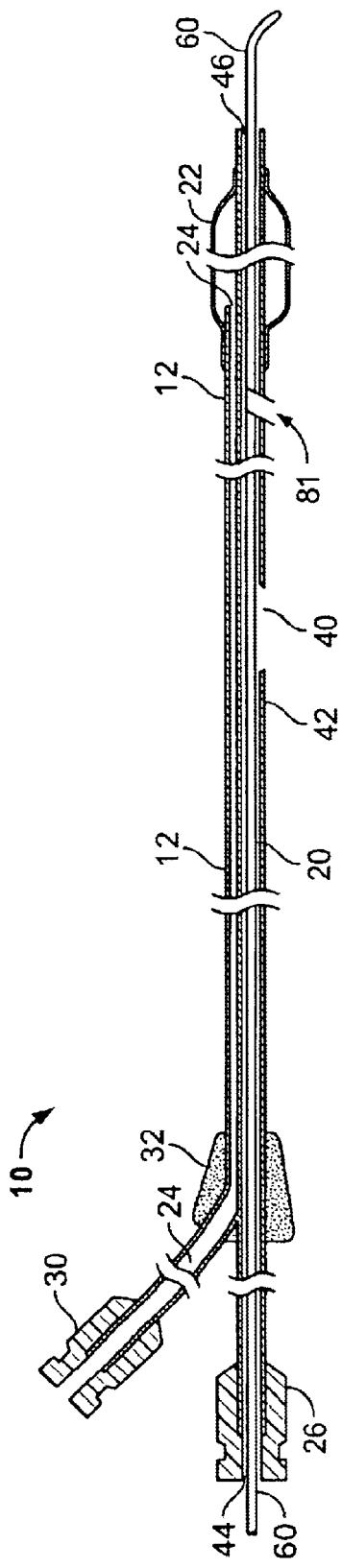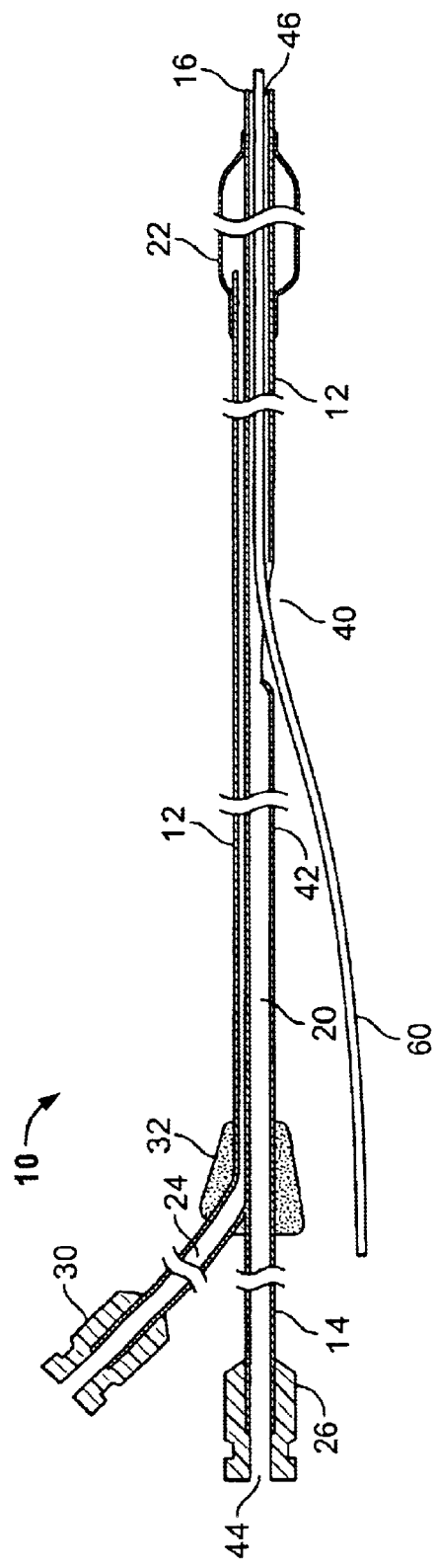
FIG. 4
FIG. 5

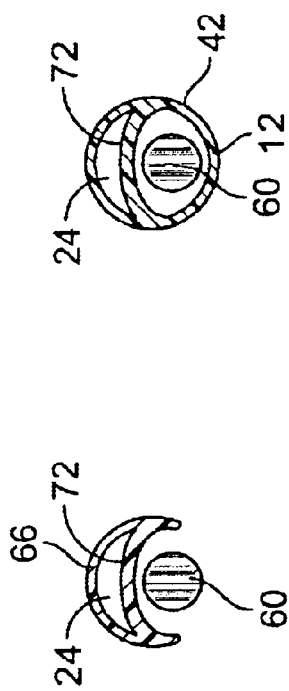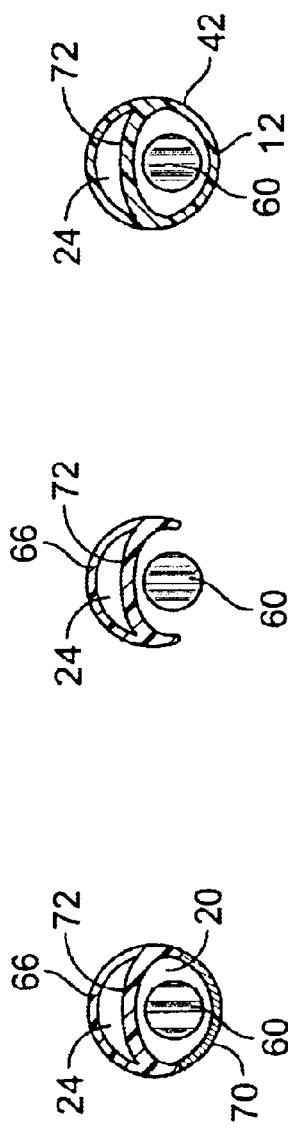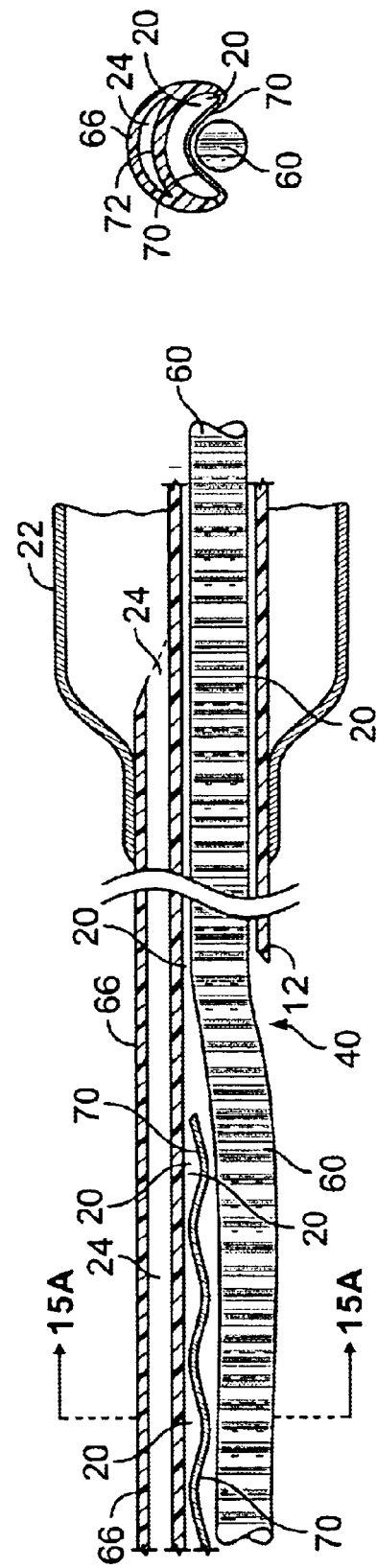

MULTI-MODE VASCULAR CATHETER SYSTEM

This invention relates to vascular catheters (such as angioplasty catheters) specially adapted for rapid exchange of both the guidewire and the catheter during use. It also relates to the method of using those catheters.

Percutaneous transluminal coronary angioplasty (PTCA) has emerged as the major viable present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion, or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter (typically 8 or 9 French size) into the aorta and coronary artery orifice. A smaller caliber catheter which has a built-in inflatable and deflatable balloon of predetermined size and diameter is passed through the guiding catheter which is positioned in the opening of a target artery. This balloon catheter (with the balloon totally deflated by negative pressure) is advanced inside the target artery toward the point of obstruction that needs to be dilated. The guidewire plays an essential role in leading the balloon catheter to the target coronary artery in safety and non-traumatic fashion. With the balloon portion of the catheter properly positioned inside the obstructed segment of the artery, under X-ray fluoroscopic observation, the balloon is inflated by injecting contrast media mixed with saline at a pressure sufficient to overcome the resistance of the arteriosclerotic plaque of the obstructed segment.

By inflating the balloon in the stenosis multiple times over a period of between 10–30 seconds and one or two minutes (allowing blood flow between inflations), the desired dilation of the obstructed segment of the artery can be achieved. When the desired results have been obtained by balloon inflations, the guiding catheter, the balloon catheter (with the balloon completely deflated with negative pressure) and the guidewire are withdrawn from the artery and the patient and the procedure is successfully terminated.

The size and diameter of the balloon to be used in a transluminal angioplasty should be approximately matched to the size and native diameter of the obstructed segment of the artery to be dilated. If the balloon size and diameter is smaller than the native artery, the results of balloon angioplasty are suboptimal, requiring a second dilation with a larger-sized balloon, and if balloon size is too large for the native artery, complications may occur due to arterial wall damage.

During the angioplasty procedure, a guidewire is first advanced into the desired location, after which the angioplasty catheter is advanced over the guidewire. It is sometimes necessary to replace (or exchange) either the guidewire or the balloon catheter during the procedure.

If the balloon is undersized, for example, the catheter must be withdrawn and replaced with a larger balloon catheter in order to permit adequate dilatation of the lesion. With conventional over-the-wire catheters, in which the guidewire lumen extends the entire length of the catheter shaft, a guidewire extension (e.g., 145 cm long) must first be attached to the regular guidewire (e.g. 175 cm long) being used outside the patient before the catheter is withdrawn. This permits the distal end of guidewire to be held in position while the catheter is removed and a new catheter is exchanged. Usually, two to three operators are needed to effect such a catheter exchange.

The catheter disclosed in U.S. Pat. No. 4,762,129 avoids the necessity for extending the guidewire or exchange guidewire (e.g. 300 cm in length) by having a short guidewire lumen that extends substantially only through the distal end of the catheter. This type of catheter is referred to herein as a rapid-exchange catheter. Thus, the guidewire is outside the catheter shaft for much of the catheter length, and is inside the catheter at only the distal end. The catheter can be exchanged without extending the 175 cm regular guidewire, and the exchange can be effected by one or two operators. However, this catheter has a serious drawback of not being able to permit ready exchange of guidewires. In clinical practice, the need for guidewire exchange is more common.

Conventional over-the-wire angioplasty catheters, with a guidewire lumen extending their entire length, permit simple guidewire exchange. During angioplasty procedures, the guidewire tip may become damaged, may be needed of a different type of guidewire or may need to be reshaped to complement the patient's vasculature. The guidewire exchange procedure is readily accomplished with such a conventional over-the-wire catheter. However, with the rapid-exchange type catheter of U.S. Pat. No. 4,762,129, guidewire exchange requires complete removal and reinsertion of both the guidewire and the angioplasty catheter; thus, defeating the original goal of expedient advantage of the rapid-exchange catheter.

Another disadvantage of the rapid-exchange catheter is backbleeding. While the guidewire is being manipulated to select the target vessel or to cross the culprit lesion, the Tuehy-Borst adapter must be loosened. This, in turn, permits backbleeding to occur.

Accordingly, there is a need for an angioplasty catheter that permits rapid-exchange of the catheter like a monorail system, and easy exchange of the guidewire like the conventional over-the-wire system. There is also a need for a catheter that will permit the user to select the mode of usage between the rapid-exchange and the over-the-wire systems.

SUMMARY OF THE INVENTION

In accordance with one aspect of the present invention, there is provided an angioplasty catheter comprising a catheter shaft having a proximal end and a distal end, an angioplasty balloon attached to the shaft at the distal end, a balloon inflation lumen extending through the shaft and communicating with the interior of the balloon, and a guidewire lumen extending through the shaft and through the balloon for receiving a steerable guidewire, wherein the guidewire lumen has a proximal opening at the proximal end of the shaft for insertion of a guidewire into the lumen, and a side port for insertion of a guidewire into the lumen through the side wall of the catheter shaft, the side port located distally of the proximal opening, the side port comprising guidewire directing means for permitting a guidewire to extend through the side port distally into the guidewire lumen and exit through the distal opening at the balloon catheter tip; while preventing a guidewire from extending through the side port proximally in retrograde fashion into the guidewire lumen. In one embodiment, the side port is located adjacent to and proximally of the balloon. In another, the side port is located proximally of the balloon within about 35 cm of the balloon. In another variation of this catheter, the side port has proximal and distal ends, and the distal end of the side port is defined by a cut into the guidewire lumen extending generally transversely with respect to the length of the catheter shaft. Preferably, the proximal end of the side port is a cut tapering proximally and outwardly from the distal end of the side port. In another variation of the foregoing catheter, the proximal end of the side port is a cut extending through the guidewire lumen extending proximally from the distal end of the side port. In a preferred embodiment, the guidewire lumen has an outside wall and the guidewire directing means comprises a guide flap having a proximal end and a distal end, the guide flap attached at its proximal end to the outside wall, with the distal end of the guide flap tapering into the guidewire lumen, and where the distal end of the guide flap is not attached to the outside wall so that a guidewire inserted distally through the side port passes over the distal end of the guide flap and into the guidewire lumen. Preferably, the guide flap is relatively flexible in comparison to the outside wall of the guidewire lumen on the distal side of the side port.

In still another variation of the catheter discussed above, the first side port is within 35 cm of the proximal end of the shaft, preferably within 30 cm, and more preferably within 20 cm.

One embodiment of the invention further comprises a perfusion opening communicating with the interior of the guidewire lumen, the perfusion opening located between the side port and the balloon.

Another aspect of the present invention is a system for performing angioplasty, comprising an angioplasty catheter having a catheter shaft, a proximal end, a distal end, an inflatable balloon at the distal end, and a guidewire lumen extending from the proximal end to the distal end, the guidewire lumen having a proximal opening and a distal opening and adapted to receive a guidewire extending the entire length of the guidewire lumen, a side port in the catheter shaft providing an opening into the guidewire lumen, the side port being located proximally of the balloon between the proximal opening and the distal opening, and a guidewire extending from outside the catheter shaft, distally through the side port, and out of the distal opening. Preferably, the side port is located within 40 cm of the balloon, more preferably within 30 or 25 cm of the balloon. In one embodiment, the side port is located inside a patient on whom an angioplasty procedure is being performed.

The present invention also includes a method for exchanging angioplasty catheters while performing angioplasty, comprising the following steps. The guidewire may be pre-loaded in the balloon catheter, before both are introduced into the guiding catheter, by inserting the distal tip of the guidewire through the side port from outside into the guidewire lumen, advancing it distally through the balloon, and coming out of the distal opening of the balloon catheter. Alternately, with the guiding catheter properly engaged in the coronary artery, the method comprises introducing a guidewire into the guiding catheter through the Tuehy-Borst adaptor (if necessary, the guidewire tip positioned inside the vascular system), deploying a balloon angioplasty catheter of the type discussed above over the proximal end of the guidewire, so that the proximal end of the guidewire extends inside the distal guidewire lumen in a retrograde fashion through the balloon, the proximal end of the guidewire coming out through the side port, thus exiting out of the guidewire lumen, while the position of the distal tip of the guidewire is maintained in a fixed position in the patient. In both methods of deploying the balloon catheter of the type being discussed, the balloon catheter shaft and the guidewire are both inside the guiding catheter lumen, but the guidewire proximal to the location of the side port is outside the balloon catheter lumen, side by side with the balloon catheter shaft, and the guidewire is inside the balloon catheter lumen on the distal side of the side port. The steps of exchanging balloon catheters consist of removing the first balloon catheter from the proximal end of the guidewire while maintaining the tip of the guidewire in the location (in the vascular system if necessary) where the operator intended, positioning a second balloon catheter according to the present invention over the proximal end of the guidewire extending proximally through the guidewire lumen, through the balloon segment and the proximal end of the guidewire, exiting through the side port of the balloon catheter, and then advancing the second balloon catheter over the pre-positioned guidewire into the vascular system.

The present invention also includes a method of exchanging a guidewire during an angioplasty procedure using the catheter of the present invention, comprising the steps of positioning a guidewire in the vascular system of a patient, providing the catheter over the guidewire so that the proximal guidewire extends proximally from the distal tip of the catheter and through the side port, advancing the catheter along the guidewire into the vascular system, removing the guidewire while maintaining the catheter in the vascular system, and inserting a second guidewire into the catheter distally through the proximal opening, through the guidewire lumen past the side port, through the balloon, and out of the distal end of the catheter.

A further method encompassed by the present invention is a method for performing balloon angioplasty, comprising the steps of providing a balloon angioplasty catheter having a catheter shaft having proximal and distal ends, a guidewire lumen through the shaft, an inflatable balloon on the catheter shaft at the distal end of the catheter, and a side-port located between the proximal end of the catheter and the balloon communicating with the interior of the guidewire lumen, inserting the catheter into a patient and blood vessel over a guidewire in the guidewire lumen, so that the guidewire extends out of the distal end of the balloon catheter while selecting a lesion, inflating balloon with the guidewire in place partially withdrawing the guidewire proximally so that the guidewire does not obstruct the side port, and inflating the balloon in a stenosis while the guidewire is partially withdrawn, so that blood can flow into the side port, distally through the guidewire lumen, and out of the distal end of the catheter while the balloon is inflated.

BRIEF DESCRIPTION OF THE DRAWINGS

FIG. 4 is a shortened schematic longitudinal section of the catheter, illustrating the guidewire inserted to provide an over-the-wire catheter mode.

FIG. 5 is a shortened schematic longitudinal section of the catheter, illustrating the guidewire inserted to provide a rapid-exchange catheter mode.

FIG. 6 is a detail of the side port section of the catheter of FIG. 4.

FIG. 14A is a transverse cross-section taken along the line 14A—14A in FIG. 14.

FIG. 14B is a transverse cross-section taken along the line 14B—14B in FIG. 14.

FIG. 14C is a transverse cross section taken along the line 14C—14C in FIG. 14.

FIG. 15 is a fragmentary longitudinal section of the catheter of FIG. 14, illustrating the guidewire passing through the side port.

FIG. 15A is a transverse cross section taken along the line 15A—15A in FIG. 15.

DETAILED DESCRIPTION OF THE INVENTION

The catheter of the present invention may be used as either a conventional-over-the-wire catheter or as a rapid-exchange catheter, and the operator may switch from one mode of use to another.

Figure 1:
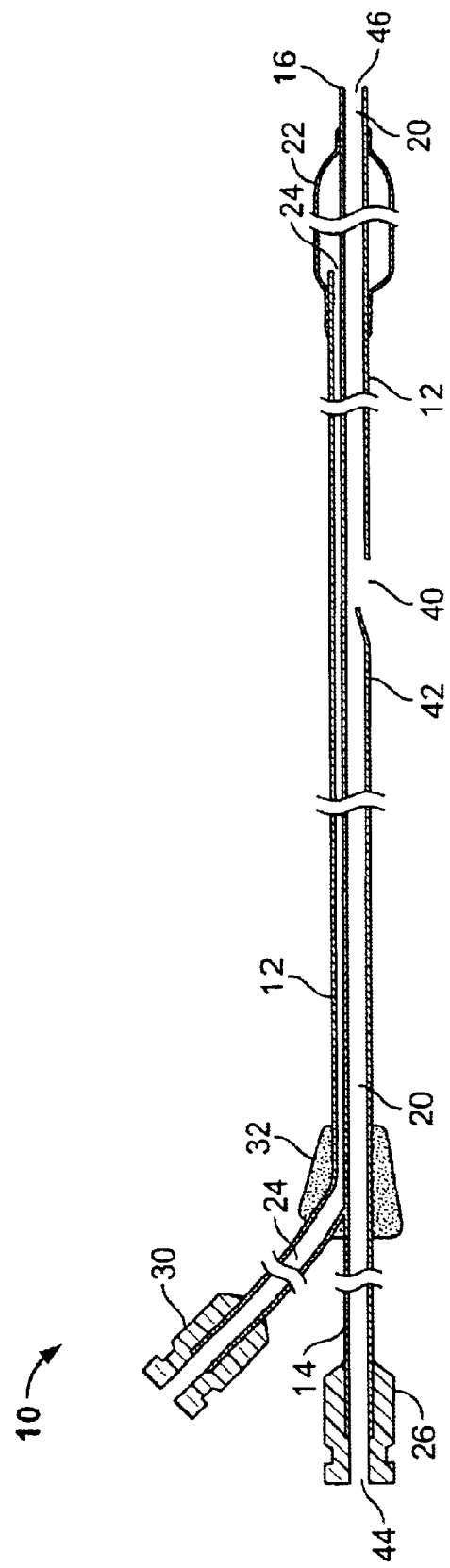
FIG. 1 is an axially shortened schematic longitudinal section of the catheter of the present invention.

FIG. 1 illustrates a schematic view of the catheter 10 of the present invention. This view is an axially-shortened longitudinal cross section of the catheter 10. The catheter 10 includes a catheter shaft 12 extending from the proximal end 14 of the catheter to the distal end 16. The catheter 10 has a guidewire lumen 20 extending the entire length of the catheter shaft 12. At the distal end 16 of the catheter shaft 12 is an angioplasty balloon 22 mounted on the catheter shaft 12. The guidewire lumen 20 extends through the angioplasty balloon 22 and terminates distally of the balloon 22 at the distal end 16 of the catheter shaft 12.

A balloon inflation lumen 24 extends the entire length of the catheter shaft 12 from the proximal end 30 into the interior of the balloon 22. The inflation lumen 24 terminates inside the angioplasty balloon 22, permitting inflation and deflation of the balloon 22.

Conventional lumen connectors 27, 31 are provided, respectively, at the proximal ends of the guidewire lumen 20 and the inflation lumen 24 in a manner that is well known. A "Y" connector 32 is also provided at the proximal end 14 of the catheter 10, somewhat distally of the lumen connectors 27, 31 at a point where the separate lumens 20, 24 converge.

The catheter 10 may be made of any conventional polymer material, such as polyethylene, polyvinylchloride, polyethylene terephthalate, or other suitable materials. Furthermore, the balloon catheter shaft of the present invention could be constructed of stainless steel, double channel hypotube, especially the shaft segment including and/or proximal to the location of the side port. The proximal shaft could, alternately, be made of single lumen stainless steel hypotube in a form of coaxial polymer sheath outside for the balloon channel.

The balloon 22 is preferably made of a non-elastomeric material so that, upon inflation, it will have a predetermined maximum inflated diameter, without substantial stretching as pressure is increased. Polymers such as PVC (polyvinylchloride) and various derivatives of polyethylene have proved to be suitable for making balloon catheters for coronary angioplasty. New polymer derivatives, including PET (polyethylene teraphthalate) and variations of Mylar material, are gaining popularity because of their high tensile strength and their potential for making very thin-walled dilation balloons. (Mylar is a trademark of Dupont, Wilmington, Del., for a polyester material.) Other suitable film-forming materials capable of withstanding pressures of 100 psi, preferably 150 psi or 200 psi, without bursting or significant stretching, may also be used to form the angioplasty balloons.

The catheter 10 of the present invention differs from conventional over-the-wire catheters by the inclusion of a specifically-shaped side port 40 extending through the outside wall 42 of the guidewire lumen 20 and into the guidewire lumen 20. The side port 40 is located distally of the proximal end 14 of the catheter shaft and the guidewire lumen connector 27 (which provides and defines a proximal opening 44 into the guidewire lumen 20). The side port 40 is preferably located proximally of the balloon 22, but may also be located distally of the balloon 22 or may be provided in vascular catheters that do not employ balloons.

In preferred embodiments the side port 40 is located within 40 cm, preferably within 30 cm or 25 cm, of the balloon 22 (on the proximal side of balloon 22). The side port 40 may advantageously be located within 20 cm, 15 cm, or even within 5 or 10 cm of the balloon 22.

The side port 40 preferably includes means for directing a guidewire through the port 40 so that the guidewire may extend distally through the port 40 and out of the distal end 16 of the catheter shaft 12, passing through the balloon 22. Thus, a guidewire may extend from outside the catheter shaft 12, through the side port 40 and distally through the guidewire lumen 20 inside the balloon 22 and finally out the distal end 16 of the catheter shaft 12. In practice, during a catheter exchange, a catheter 10 is removed from the guidewire by pulling it off of the proximal end of the guidewire. A new catheter 10 is then placed on the guidewire by inserting the proximal end of the guidewire into the distal opening 46 of the guidewire lumen 20, extending the guidewire proximally through the balloon to the side port 40, and then out of the side port 40.

If the catheter 10 is to be used as a conventional over-the-wire catheter, then the guidewire is inserted through the proximal opening 44 of the guidewire lumen 20 and is advanced distally through the guidewire lumen 20 past the side port 40, through the balloon 22, and out of the distal opening 46 of the guidewire lumen 20. Other modes of usage are described in more detail below.

In order to facilitate use of the catheter 10 in the manner described, the side port 40 is provided with means for permitting a guidewire to extend through the side port 40 distally into the guidewire lumen 20, while preventing a guidewire from extending from outside the catheter shaft 12 through the side port 40 and thence proximally into the guidewire lumen 20. Thus, when a guidewire is advanced through the proximal opening 44 of the guidewire lumen 20, the side port 40 should be configured to avoid exiting of the guidewire out of the side port 40 as the guidewire advances distally.

Figure 2:
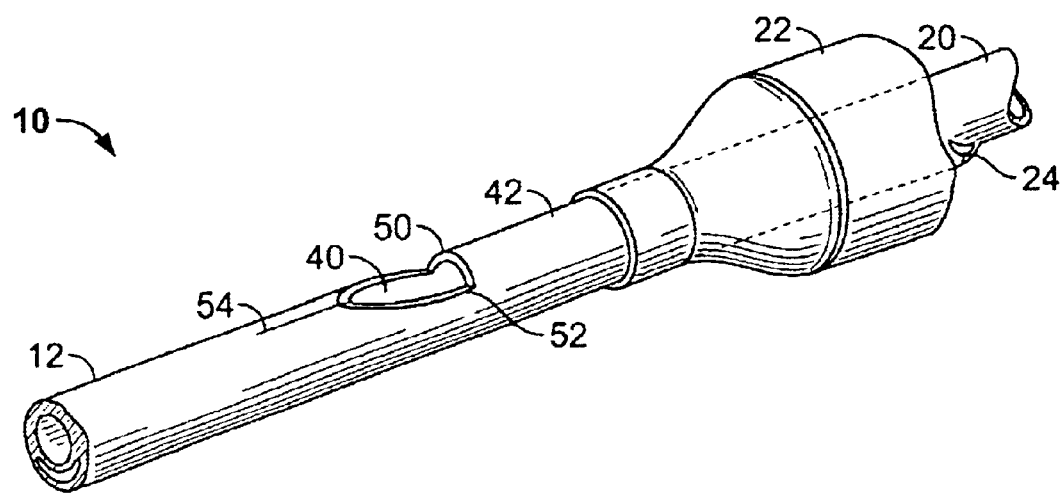
FIG. 2 is a perspective view of a portion of the catheter of FIG. 1, illustrating one embodiment of the side port.

The means for directing the guidewire at side port 40 may take one of several forms. One example is illustrated in FIG. 2. In FIG. 2, the catheter shaft 12 is cut at the side port 40 to provide an opening into the guidewire lumen 20. In the embodiment illustrated in FIG. 2, the side port 40 is defined by a distal cut 50 at the distal end of the port 40 and by a proximal cut 52 exiting proximally from the distal cut 50. In the FIG. 2 embodiment, the distal cut 50 extends radially down into the guidewire lumen 20 through the outside wall 42 of the guidewire lumen 20 in a direction generally transverse to the length of the catheter shaft 12. In other words, the distal cut 50 extends radially inward from outside the catheter shaft 12 through at least a portion of the outside wall 42 of the guidewire lumen 20. Alternatively, this cut could be slanted.

The proximal cut 52 may advantageously extend from the deepest part of the distal cut 50, tapering radially outwardly through the outside wall 42 of the guidewire lumen as the proximal cut 52 extends proximally along the catheter shaft 12. Thus, the port 40 in FIG. 2 is defined by a proximal cut 52 tapering into the guidewire lumen 20 as it extends distally and a distal cut 50 extending radially into the guidewire lumen 20, so that the side port 40 is in the form of a notch.

In one preferred embodiment, a slit 54 is provided extending longitudinally (axially) in a proximal direction from the proximal end of the proximal cut 52 through the outside wall 42 of the guidewire lumen 20.

The geometry of the side port 40 illustrated in FIG. 2 permits easy distal insertion of the guidewire through the side port 40, and also permits a guidewire inserted into the distal end opening 46 of the guidewire lumen 20 to be readily directed out of the guidewire lumen 20 at the side port 40. The slit 54 avoids undesired junctional bending of the guidewire as it traverses side port 40.

The side port 40 of the present invention may be distinguished from perfusion holes provided in prior art catheter by its size. The side port 40 (unlike perfusion holes in prior art catheters) is large enough as a guidewire gate to permit the guidewire to easily be inserted through the side port 40. This is in sharp distinction to prior art perfusion holes, which were sized to prevent passage of the guidewire and were typically provided as multiple small holes in the catheter shaft 12. It should be understood that the guidewire directing elements of the side port 40 are preferred, but not essential elements of the invention.

It should also be understood that the catheter shaft 12 may be made of a single material or may be made of different materials bonded or otherwise joined together. Distal portions of the catheter 10 may be made of different materials than proximal portions; alternatively, one lumen of the catheter may be made of different material than another lumen. The balloon lumen, for example, could be made of relatively stiff material to provide improved pushability, while the guidewire lumen may be defined by relatively flexible material, or vice versa.

Figure 3:
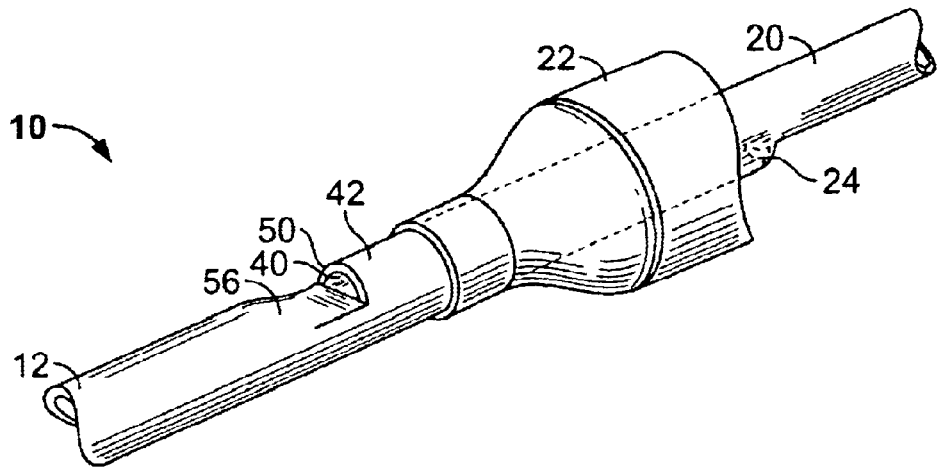
FIG. 3 is a perspective view of a portion of the catheter as in FIG. 2, illustrating another embodiment of the side port.

An alternative embodiment of the side port 40 is illustrated in FIG. 3. In this embodiment, the port 40 is defined at its distal end by a distal cut 50 extending generally radially inward into the guidewire lumen 20. A flexible apron 56 is attached to the outside wall 42 of the guidewire lumen 20 at the proximal end of the side port 40. This apron is a flap attached at its proximal end to the catheter shaft 12 and extending distally into the opening of the port 40. The apron 56 is unattached at its distal end. The apron 56 is preferably made of material at least as flexible as the outer wall 42 of the guidewire lumen 20; however, it is preferably more flexible than the outer wall 42 of the guidewire lumen 20 or the catheter shaft 12.

The side port 40 in FIG. 3 functions in the same manner as described in connection with FIG. 2 to permit a guidewire to extend distally from outside the catheter shaft 12 into the side port 40, while preventing a guidewire extending the entire length of the guidewire lumen 20 from exiting through side port 40 as it progresses distally through the guidewire lumen 20. The configuration of the side port 40 in FIG. 3 also permits a guidewire to be introduced into the distal opening 46 of the guidewire lumen 20, the guidewire to be advanced proximally through the guidewire lumen traversing the balloon 22, and to exit out of the side port 40 after it has traversed the section of the guidewire lumen 20 inside the balloon 22.

In another embodiment, the shape and feature of the side port 40 could be molded in contrast to cutting out the opening. With the basic opening provided, the refinements of the side port 40 could be shaped and trimmed by the molding technique of polymer.

The use of the catheter 10 of the present invention as a conventional over-the-wire catheter is further illustrated in FIG. 4.

FIG. 4 illustrates the catheter of FIG. 1 with a guidewire 60 extending the entire length of the guidewire lumen 20 from the proximal opening 44 through the balloon 22 and out of the distal opening 46 of the guidewire lumen 20. The guidewire 60 extends past the side port 40 but does not exit through the port 40 as it is being advanced distally through the guidewire lumen 20, because of the configuration of the side port 40 and partly due to guidewire manipulation under fluoroscopy. Some care and attention on the part of the physician will also be necessary to avoid inadvertent exit of the guidewire out of the side port 40 in this situation, by careful fluoroscopic observation made during the passage of the guidewire tip in the vicinity of the side port 40.

FIG. 5 illustrates the catheter 10 of FIG. 1 with the guidewire 60 extending distally from outside of the catheter 10 through the side port 40, thence distally through the guidewire lumen 20 through the balloon 22 and out of the distal opening 46 of the guidewire lumen 20.

FIG. 6 is a detail of the catheter 10 in the vicinity of the side port 40. FIG. 6 shows the guidewire 60 extending through the guidewire lumen 20 from the proximal end 14 of the catheter 10, past the side port 40 (while remaining inside the guidewire lumen 20), and through the balloon 22.

Figure 6C:
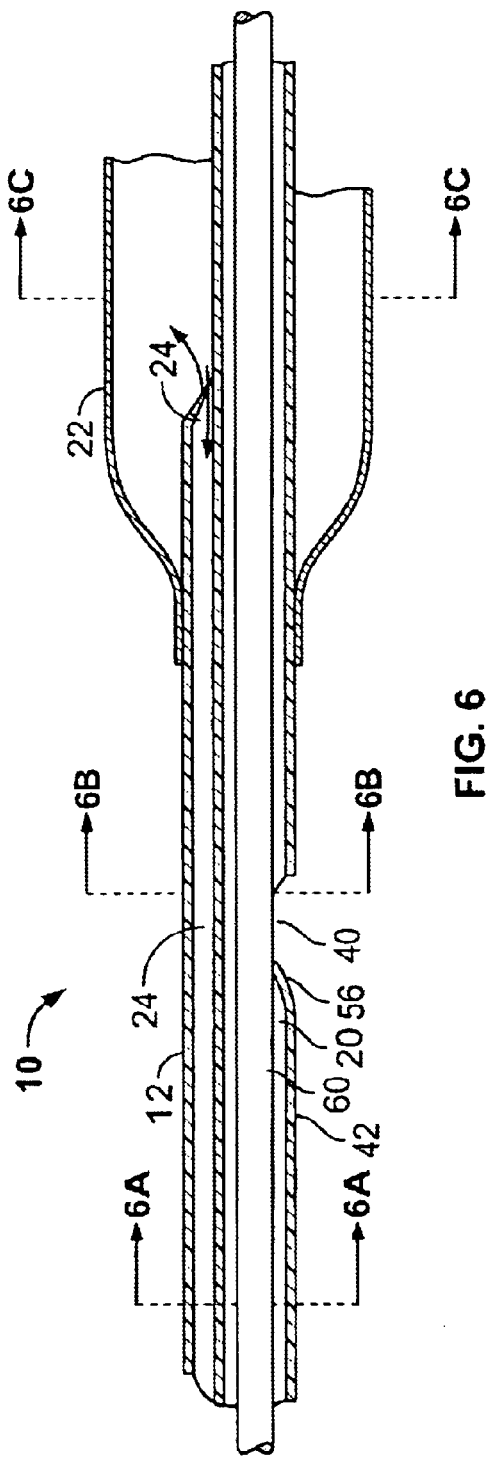
FIG. 6C is a transverse cross section taken along the line 6C—6C in FIG. 6.
Figure 6C:
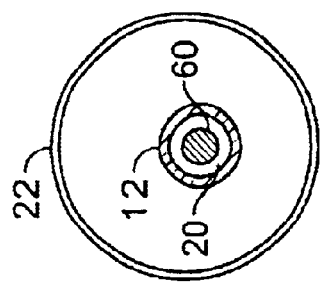
Figure 6B:
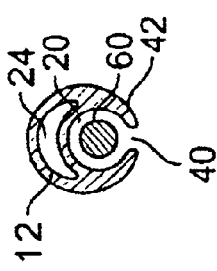
FIG. 6B is a transverse cross section taken along the line 6B—6B in FIG. 6.
Figure 6A:
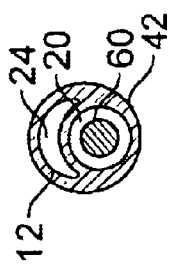
FIG. 6A is a transverse cross section taken along the line 6A—6A in FIG. 6.

FIG. 6a shows the guidewire 60 inside the guidewire lumen 20 at a point proximally of the side port 40.

FIG. 6b shows the guidewire 60 at the side port 40 and illustrates the opening through the outer wall 42 of the guidewire lumen 20 and the guidewire inside the lumen 20.

FIG. 6c illustrates the guidewire 60 inside the guidewire lumen 20 as it traverses the length of the balloon 22.

Figure 7:
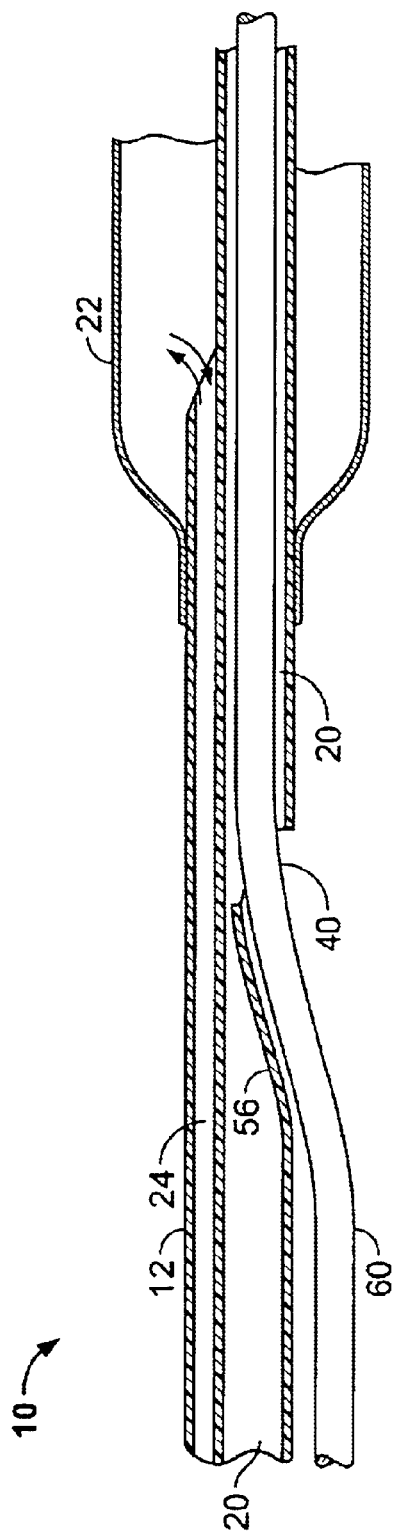
FIG. 7 is a detail of the side port section of the catheter of FIG. 5.

FIG. 7 illustrates the catheter 10 of FIG. 5 in the vicinity of the side port 40 with the guidewire 60 in place. Note that on the proximal side of the side port 40, the guidewire 60 is outside of the catheter shaft 12, paralleling with the empty guidewire lumen that is proximal to the junctional side port 40. The guidewire enters into the catheter shaft 12 and into the guidewire lumen 20 at the side port 40 as the wire extends distally. Distally from the side port 40, the guidewire traverses the distal portion of the catheter shaft 12 inside of the guidewire lumen 20 extending through the balloon 22.

Note that the apron 56 illustrated in FIG. 7 permits ready insertion of the guidewire 60 through the side port 40 when the wire is extending from outside and into the side port 40 distally through the balloon 22, and similarly the apron 56 permits the guidewire 60 to readily come out through the side port 40, when the guidewire 60 is inserted into the distal opening 46 of the guidewire lumen 20 and is advanced proximally inside the guidewire lumen 20 through the balloon 22.

Figure 8:
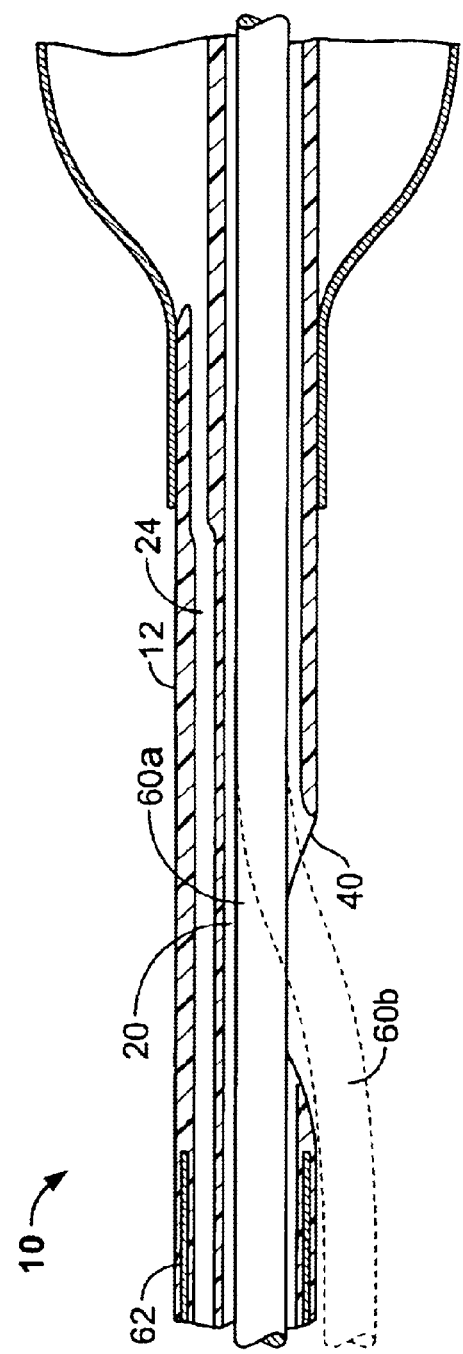
FIG. 8 is a composite detail of the side port section of another embodiment of the catheter of FIG. 4.

Another embodiment of the invention is illustrated in FIG. 8. FIG. 8 is a closeup detail of the catheter shaft 12 in the vicinity of the side port 40, showing a guidewire 60a extending the entire length of the guidewire lumen 20, and also illustrating in phantom (60b) the alternative insertion of the guidewire 60 through the side port 40.

In the embodiment illustrated in FIG. 8, the catheter shaft 12 on the proximal side of the port 40 is made of a different material than the remaining distal portion of the catheter shaft 12. Specifically, the proximal portion 62 of the catheter shaft 12 is made of a relatively stiff material. The proximal portion 62 of the catheter shaft 12 may, for example, comprise a hypotube. A hypotube is a thin walled tube of metal, preferably stainless steel. Alternatively, the proximal portion 62 of the catheter shaft 12 may comprise a plastic-coated spiral wound wire or ribbon of metal. This later structure has superior flexibility (in comparison to hypotube) while maintaining pushability.

Figure 9:
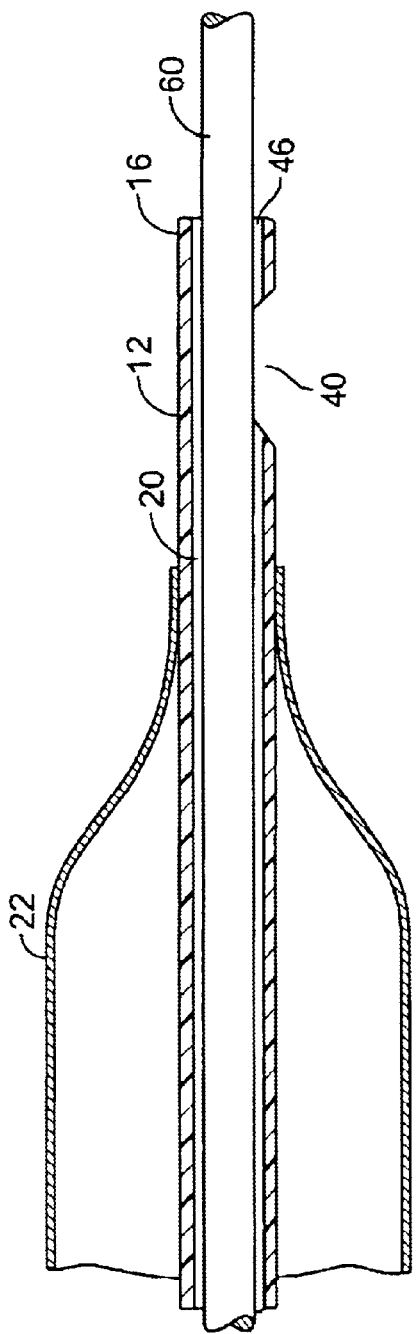
FIG. 9 is a detail of the side port section of another embodiment of the catheter of the present invention, illustrating the guidewire extending through the length of the guidewire lumen.

Although much of the disclosure has emphasized the location of the side port 40 proximally of the balloon 22, the side port 40 may also be located distally of the balloon 22. FIG. 9 illustrates location of the side port 40 distally of the balloon 22 but proximal to the distal end 16 of the catheter 10. In the illustrated embodiment, the guidewire 60 is inside the guidewire lumen 20 extending from the proximal opening 44 to the distal opening 46, passing through the balloon 22 and passing by the side port 40 (and not exiting through the side port 40). This distal side port 40 may be in place of the previously-described side port 40 located proximally of the balloon 22, or in addition to the proximal side port 40. This distal side port 40 design may be especially useful in catheters other than balloon catheters, such as catheters used in laser procedures, atherectomy catheters, stent deployment catheters, or intravascular imaging catheters.

Figure 10:
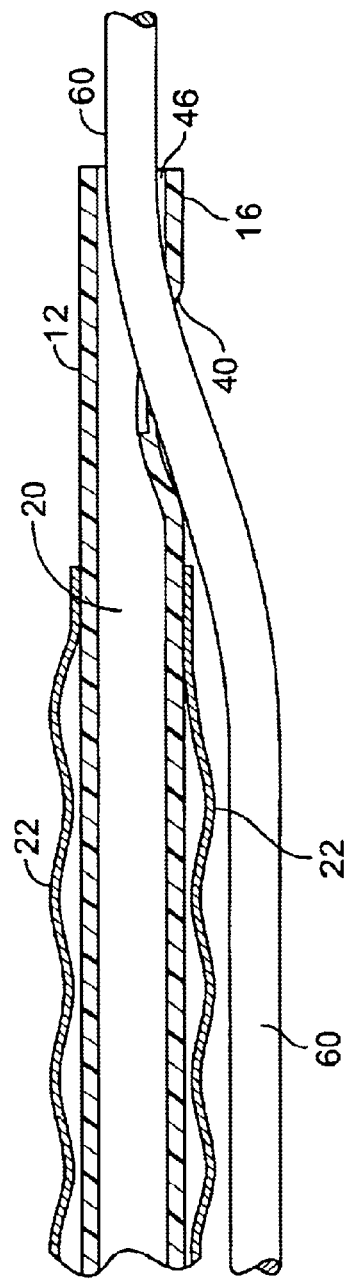
FIG. 10 corresponds to FIG. 9, except that the guidewire extends through the side port.

FIG. 10 corresponds to the embodiment of FIG. 9, except that the guidewire 60 is extending through the side port 40 in an antegrade fashion by entering the guidewire lumen 20 from outside of the catheter 10 and exiting out of the distal opening 46 of the catheter 10. The proximal segment of the guidewire 60 lies adjacent to and outside of the catheter 10 and the deflated balloon 22. This illustration depicts the rapid-exchange mode of deployment of the catheter of FIG. 9. It should be understood that the balloon can be inflated and stenoses dilated even with the guidewire 60 located outside of the balloon 22. If desired, the guidewire may instead be withdrawn during balloon inflation, so that the wire is not in contact with the balloon 22 during inflation.

It should be further noted that, in preferred embodiments, the side port 40 is within 40 cm of the distal end of the catheter 10, preferably within 30 or 20 cm of the distal end, and optionally within 10 or 5 cm of the distal end of the catheter shaft. Moreover, it is contemplated that the catheters of the present invention may be provided with more than one side port 40.

Figure 11:
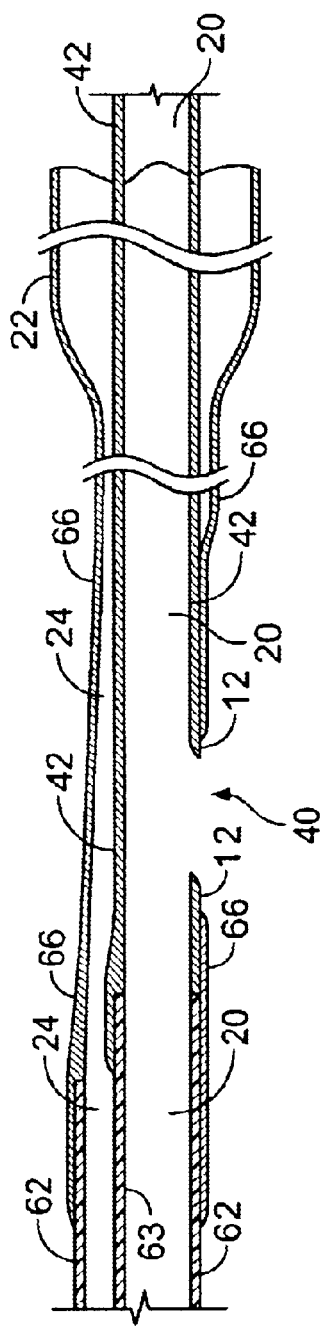
FIG. 11 is a longitudinal section of the guide port portion of still another catheter according to the present invention.

FIG. 11 illustrates a related structure, illustrating the use of different materials in the vicinity of the side port 40 of catheter 10. The proximal portion 62 of the catheter shaft 12 is made of a non-bioactive metal, such as stainless steel hypotube. The hypotube has a dual lumen; that is, there is a septum 63 dividing the guidewire lumen 20 from the balloon inflation lumen 24. This double lumen metal hypotube ends adjacent to and proximal of the side port 40. The side port 40 itself is made of a polymer tube forming the catheter shaft 12 which is directly bonded to the distal end of the proximal portion of the shaft 62 (which in this instance is made of metal). At the point where the proximal portion 62 of the catheter shaft 12 meets the distal portion 64 of the catheter shaft 12, a metal-to-plastic bond must be formed. In the embodiment illustrated in FIG. 11, the outside wall 42 of the guidewire lumen 20 is a continuous tube located inside of and coaxially with an outer tube 66 which is the outer wall of the balloon inflation lumen 24. Thus, at the side port 40 and at points distal thereto, the guidewire lumen 20 is located coaxially and concentrically inside of the balloon inflation lumen 24. On the side of the catheter shaft 12 where the side port 40 is located, the outer wall 66 of the balloon inflation lumen 24 is bonded to the outside wall 42 around the perimeter of the side port margins of the guidewire lumen 20. Distally of the side port 40, however, the walls 66, 42 are not bonded together, and the outer wall 42 of the guidewire lumen is located inside of but generally separated from the outer wall 66 of the balloon inflation lumen. The outer wall 66 of the guidewire lumen 24 is blown to form the balloon 22.

Figure 12:
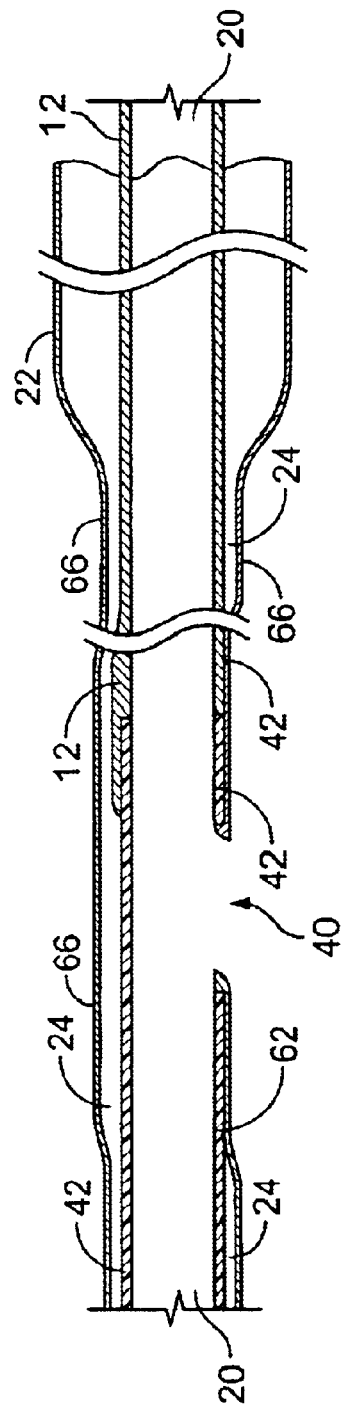
FIG. 12 is a longitudinal section of the side port portion of a different catheter according to the present invention.

FIG. 12 illustrates still another embodiment of the side port 40 section of the catheter shaft 12. The catheter shaft is made of two coaxial tubes, one comprising the outside wall 42 of the guidewire lumen, and the other comprising the outer wall 66 of the balloon inflation lumen 24. In this embodiment, the wall 66 of the balloon inflation lumen 24 may advantageously be made from a polymer material extending both proximally and distally of the side port 40.

In the embodiment illustrated in FIG. 12, the wall 42 of the guidewire lumen 20 is formed of a rigid material such as metal hypotube, extending up to the side port 40 and a short distance beyond the side port 40. The inflation lumen 24 surrounds the wall 42 of the guidewire lumen 20. The balloon lumen 24 and the guidewire lumen 20 may thus be considered as concentric tubes.

In the vicinity of the side port 40, the outer wall 66 of the balloon inflation lumen 24 is joined to the side of the wall 42 of the guidewire lumen on the side of the catheter shaft 12 in which the side port 40 is formed. This prevents leakage out of the balloon inflation lumen 24. In the FIG. 12 embodiment, because the side port 40 is formed in a relatively rigid material such as metal, softer polymer material (such as the material making up the outer wall 66 of the balloon inflation lumen 24) may line the opening of the side port 40. This softer polymer material may also form an apron as illustrated in FIG. 3 and FIG. 7.

In the embodiment illustrated in FIG. 12, at a point distal to the side port 40, the wall 42 of the guidewire lumen changes from metal to polymer material. This may be done by conventionally sealing a polymer tube to the end of or over the end of the proximal portion 62 of the metal tube defining the guidewire lumen 24.

The balloon 22 may be blown from the same tube which defines the outer wall 66 of the balloon inflation lumen 24.

Figure 13:
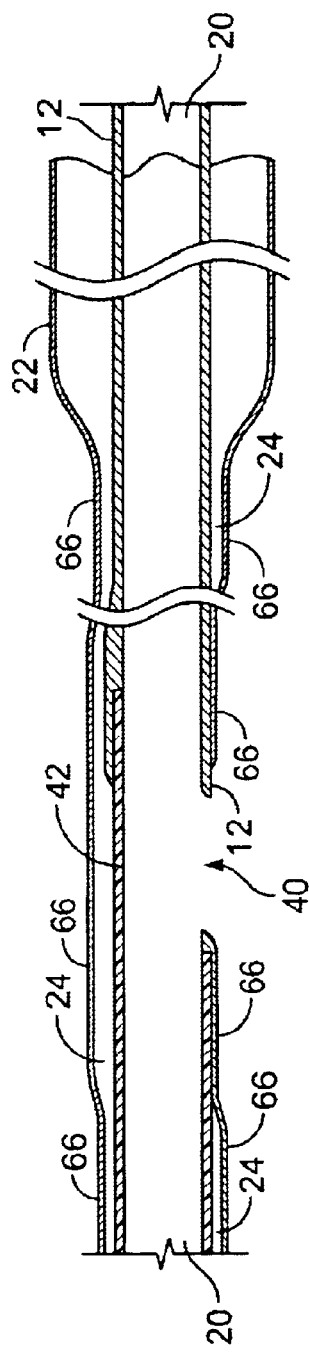
FIG. 13 is a longitudinal section of the side port portion of yet another catheter according to the present invention.

FIG. 13 is similar to FIG. 12, except that in the embodiment of FIG. 13, the metal hypotube forming the proximal portion 62 of the wall 42 of the guidewire lumen 24 is cut longitudinally in the vicinity of the side port 40. In this manner, the side port 40 may be completely formed from polymer material, or only the proximal portion of the side port 40 may be metal hypotube (or other relatively rigid material). The portion of the catheter shaft distal to the side port 40 is formed of polymer material, except that the wall 42 of the guidewire lumen 20 opposite of the side port 40 may be metal extending the length of or slightly past the side port 40. Having the metal extend distally past the side port 40 will decrease the possibility of buckling in the vicinity of the side port 40 when the catheter is pushed along the guidewire 60. In the FIG. 13 embodiment, the outer wall 66 of the balloon inflation lumen 24 is bonded to the wall 42 of the guidewire lumen around the side port 40. In other locations, however, the guidewire lumen 20 is located concentrically inside the balloon inflation lumen 24.

In an alternative embodiment, a plastic tube may be placed inside the metal hypotube to form one lumen of the catheter (either the balloon inflation lumen or the guidewire lumen). Similarly, it is contemplated that a transition from side by side lumens to coaxial lumens may occur in the vicinity of the side port 40, so that coaxial lumens are used proximally or distally of the side port 40 and side by side lumens are used in the other direction from the side port 40.

It is further contemplated that a stylet may be inserted into the proximal portion 62 of the catheter shaft in any of the embodiments of the invention when the catheter is used as a rapid-exchange catheter. Preferably, the stylet would extend from the proximal opening 44 of the guidewire lumen 20 up to the vicinity of the side port 40 to provide improved pushability of the catheter. The stylet is made of relatively rigid material, such as rigid polymer or metal.

In another alternative approach the proximal protion 62 of the catheter shaft 12 can be metal that extends distally past the site of the side port 40. The metal part of the catheter shaft 12 can extend only to the opposite side of the shaft 12 from the wall 42 of the guidewire lumen 20, extending distally beyond the side port 40. In this embodiment, the half of the shaft 12 on the side port 40 side could be made of flexible polymer material, whereas the opposite half of the shaft 12 is a metal part; thus, preventing bending or weakening of the catheter shaft 12 at the site of side port 40. In another embodiment, the proximal portion 62 of the shaft 12 can be a metal hypotube that extends distally of the side port 40 in full circumferential fashion, so that the side port 40 could be directly cut through the metallic wall, which is equivalent of shaft wall 42 of the FIG. 1. (See, e.g., FIG. 12.)

In yet other embodiments, the proximal portion 62 of catheter shaft 12 may be formed of a more rigid polymer, or may be stiffened with an embedded stiffening member, such as a wire or metal ribbon.

The reason for utilizing stiffer materials to form the proximal portion 62 of the catheter shaft 12 is to facilitate the pushability of the catheter 10 when the guidewire 60 is utilized by entering distally through the side port 40.

Figure 14:
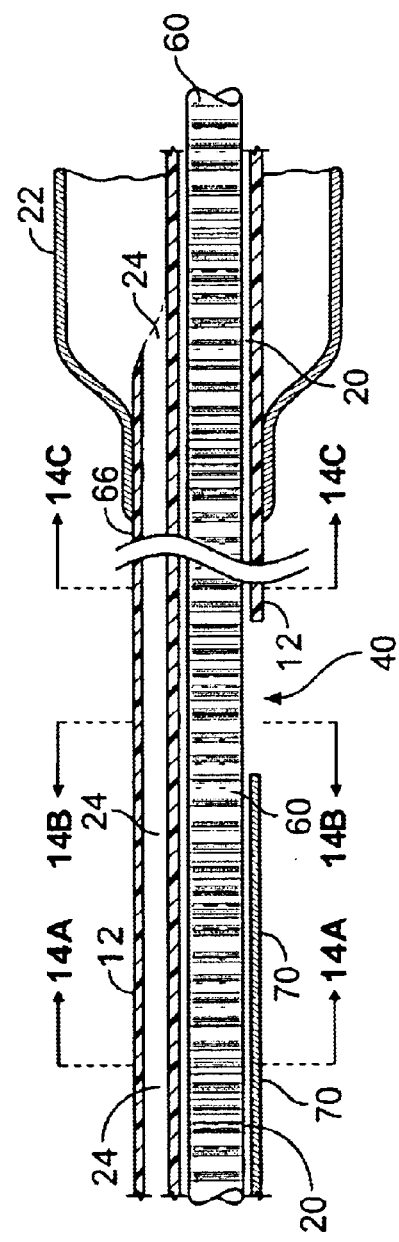
FIG. 14 is a fragmentary longitudinal section of the side port portion of a catheter according to the present invention which has a collapsible lumen.

FIG. 14 illustrates an embodiment of the catheter of the present invention in which the catheter shaft 12 proximally of the side port 40 includes a collapsible wall 70 forming the outer wall of the guidewire lumen 20. The guidewire 60 extends through the guidewire lumen 20 passing by the side port 40 (in the embodiment illustrated in FIG. 14) but not extending through the side port 40. Instead the guidewire 60 continues in the guidewire lumen 20 past the side port 40 and extends through the balloon 22. In this over-the-wire mode of use, the collapsible wall 70 is expanded passively outward by the guidewire 60 inside the guidewire lumen 20. The collapsible wall 70 may collapse inward when its lumen is empty or may even be molded or extruded in a collapsed configuration. However, it preferably is made of a high tensile strength polymer material that does not stretch during use.

The portion of the catheter shaft 12 opposite the collapsible wall 70 is preferably made of a relatively rigid (e.g., high density) polymer to provide desired pushability characteristics.

The construction of the catheter illustrated in FIG. 14 may be more fully understood by reference to the cross sections, FIGS. 14A, 14B, and 14C. In these illustrations, the outer wall 66 of the balloon inflation lumen is formed of a thicker or more rigid polymer material (or other suitable material) than the collapsible wall 70. As is shown in the cross sections, the inner wall 72 of the balloon inflation lumen 24 (which may also be a common wall with the guidewire lumen 20) is also a thicker or more rigid material than the collapsible wall 70. Note that the collapsible wall 70 is not present in FIG. 14B, which is taken through the side port 40, and that the outside wall 42 of the guidewire lumen 20 is formed of more rigid material in cross section 14C, which is taken distal to the side port 40, so there is no collapsible wall 70 distal of the side port 40.

FIG. 15 illustrates the catheter of FIG. 14 with the guidewire 60 inserted in the speed-exchange mode. Thus, proximal to the side port 40, the guidewire 60 is outside the catheter shaft 12 and outside the guidewire lumen 20. The guidewire 60 passes through the side port 40 and is inside the guidewire lumen 20 distal to the side port 40. In FIG. 15, the collapsible wall 70 is collapsed inwardly toward the inner wall 72 of the balloon lumen 24. This is further illustrated in the cross section, FIG. 15A, showing the guidewire 60 adjacent to the collapsible wall 70 proximal to the side port 40.

The primary purpose of the collapsible wall 70 is to minimize the cross sectional profile of the catheter shaft 12 when the proximal portion 62 of the catheter shaft 12 is positioned side by side with the guidewire 60 inside the limited cross sectional space of the guiding catheter, during rapid-exchange use of the catheter 10. It should be noted that this collapsible wall concept is also applicable to other applications of intravascular and nonvascular catheters.

1) Summary of Different Modes for Using the Catheter

It should be apparent from the foregoing detailed description of the catheter itself that it can be used in a number of different manners. Specifically, it can be used in the following different modes:

a) as a rapid-exchange catheter b) as an over-the-wire catheter c) to switch from rapid-exchange mode to over-the-wire mode d) to switch from over-the-wire mode to rapid-exchange mode e) to exchange rapid-exchange mode with rapid-exchange mode f) to exchange over-the-wire mode with over-the-wire mode g) to provide guidewire exchange capability in both rapid-exchange mode and over-the-wire mode h) potentially as a perfusion catheter.

2) Use as a Rapid-Exchange Catheter

The method of using this catheter in rapid-exchange mode is similar to the method of conventional rapid-exchange catheter. The guidewire is introduced through the Tuehy-Borst adapter that is connected to the distal end of the guiding catheter. When the guidewire is in place in the guiding catheter, the multi-mode balloon catheter 10 of the present invention is engaged over the proximal end of the guidewire 60, by inserting the proximal end of the guidewire 60 through the distal opening 46 of the guidewire lumen 20. The proximal guidewire tip is advanced proximally through the balloon 22 and then out of the side port 40. Once the multi-mode balloon catheter 10 is properly engaged over the guidewire 60 in this manner, the balloon catheter is advanced through the Tuehy-Borst adapter of the guiding catheter. The guidewire and the balloon catheter could be advanced together as a unit or independently of each other, carefully securing the guidewire tip to always remain inside the distal guidewire lumen or inside the vessel and the insuring that the guidewire tip does not disengage from side port 40.

Alternately, the guidewire could be pre-loaded in the balloon catheter by advancing the guidewire tip through the side port 40 so that the guidewire enters the guidewire lumen 20, passing through the balloon catheter tip 16. Then the guidewire 60 is pre-loaded in the balloon catheter shaft 12, and then the balloon catheter 10 and guidewire 60 are both inserted together into the guiding catheter.

If the balloon catheter 10 needs to be replaced, the procedure is exactly reversed. Without using an extension wire or exchange wire, the first multi-mode catheter 10 is removed from the guidewire 60, keeping the tip of guidewire 60 in the same location. When the first catheter 10 has been removed, the second catheter 10 is inserted by repeating the balloon catheter engagement procedure discussed above.

3) Use as a Conventional Over-the-Wire Catheter

In this mode, the guidewire 60 is usually engaged inside the guidewire lumen 20 that runs through the entire length of the catheter shaft 12, tip to tip. The side port 40 on the distal portion of the catheter shaft 12 is completely avoided, making sure that the guidewire distal tip does not go out through the side port 40. Then, the balloon catheter 10 (the Multi-mode Catheter) is inserted through the Tuehy-Borst adapter of the guiding catheter and advanced forward distally inside the guiding catheter. Before entering the coronary vessel, the tip of the guidewire 60 is extended sufficiently beyond the distal end 16 of the balloon catheter 10, as safety and vessel entry considerations dictate.

If the first catheter needs to be replaced or exchanged during the angioplasty procedure, this over-the-wire mode will require a guidewire extension, exactly like the conventional over-the-wire system, but the second balloon catheter could be deployed in the rapid-exchange catheter mode, thus, avoiding the use of extension wire during the deployment of the catheter exchange.

If there is a need for guidewire exchange, there would be no problem replacing it in the same manner as with a conventional over-the-wire system. The first wire is pulled out, and a new wire is introduced through the proximal opening 44 of the balloon catheter 10. One must ensure that the guidewire tip does not pass through the side port 40 during this guidewire 60 replacement maneuver. This can easily be achieved by careful fluoroscopic observation and proper steering of the "J" shaped guidewire tip, and by keeping the side port 40 segment of the balloon catheter shaft 12 in the straight portion of the guiding catheter.

4) Changing from Rapid-Exchange Mode to Over-the-Wire Mode

The procedure of using the rapid-exchange mode with the multi-mode catheter 10 is already discussed in section 2) above. The procedure of switching the catheter from rapid-exchange mode to over-the-wire mode will be discussed next.

While the catheter 10 is in place as a rapid-exchange catheter, the guidewire 60 is pulled completely out of the guidewire lumen 20 through the side port 40 and out of the guiding catheter through the Tuehy-Borst adapter, while keeping the balloon catheter 10 in place without moving the distal end 16. Next, the guidewire 60 is inserted through the proximal opening 44 of the guidewire lumen 20 of the catheter 10, in exactly the same fashion as explained above in connection with the conventional over-the-wire catheter mode. When the tip (which has usually a "J" shape for directional guidance) of the guidewire 60 reaches the region of the side port 40, the guidewire tip is carefully steered under fluoroscopy, so that the tip of the guidewire leads toward and into the distal guidewire lumen 20 of the balloon catheter, avoiding extrusion of the tip through the side port 40. This completes the conversion from rapid-exchange mode into the over-the-wire mode.

5) Conversion from Over-the-Wire Mode to Rapid-Exchange Mode

Before the multi-mode catheter is inserted into the guiding catheter, the guidewire 60 is placed inside the balloon catheter 10. This is accomplished by inserting the guidewire 60 through the proximal opening 44 of the guidewire lumen 20 and advancing it toward the distal tip of the balloon catheter, making sure that the guidewire tip does not exit out of the side port 40. The guidewire tip is then pulled back a safe distance (e.g. 5–10 cm) from the distal end 16, in order to prevent damage of the guidewire tip during inserting the balloon catheter into the Tuehy-Borst adapter of the guiding catheter.

Prior to reaching the very distal end of the guiding catheter, the guidewire 60 is advanced forward out through the distal opening 46 of the guidewire lumen 20, so that the tip of guidewire protrudes from the distal end 16 of the catheter 10 a sufficient distance to permit safe steering and guidance of the balloon catheter 10 inside the coronary artery.

Switching to rapid-exchange mode from the over-the-wire mode has two potential applications. The first scenario is to convert into rapid-exchange mode with a new or different sized multi-mode balloon catheter, and the second scenario is to convert the same catheter into the rapid-exchange mode. The first scenario is more likely in practice, while the second scenario may have a limited need in practice.

In order to switch to rapid-exchange mode, the guidewire 60 is extended, using the extender wire and coupling the two segments together. After pulling the balloon catheter 10 over the extended guidewire out of the guiding catheter, the extender wire is uncoupled, disconnecting the extender wire from the main guidewire 60 in place. Then the newly prepared multi-mode balloon catheter 10 is advanced over the guidewire 60 so that the proximal end of the guidewire enters the distal opening 46 of the guidewire lumen 20, and then the guidewire extends out through the side port 40. This completes the conversion into rapid-exchange mode.

6) Use of Two Consecutive Multi-Mode Catheters in Over-the-Wire Mode

In this scenario the two multi-mode balloon catheters are simply used in over-the-wire mode in a consecutive manner.

The catheter exchange procedure is exactly the same as any conventional over-the-wire catheter exchange. However, attention should be paid so that the distal tip of the guidewire 60 does not exit through the side port 40 but stays in guidewire lumen 20 and comes out through the distal opening 46. This can be achieved by simple fluoroscopic observation and steering the "J" tip of the guidewire. This procedure is also discussed in the section (3) earlier.

7) Use of Two Consecutive Multi-Mode Catheters in Rapid-Exchange Mode

Similar to the scenario in section (6) above, this is a simple situation in which two multi-mode balloon catheters are used consecutively in rapid-exchange mode. The technical procedure of using this catheter in rapid-exchange mode is already discussed in the section (2) earlier.

8) Guidewire Exchange Capability in Rapid-Exchange Mode of Use

One of the severe limitations of the existing rapid-exchange catheter systems is that the guidewire cannot be exchanged freely. If the guidewire is damaged, needs to be reshaped, or if the physician requires a different wire, then the guidewire and the balloon catheter must be withdrawn completely out of the patient and then start all over again. In this situation, which occurs quite often with complex angioplasty procedures, the main benefit of rapid-exchange catheter system is negated.

With catheter system of the present invention, this very severe limitation of the conventional rapid-exchange system is overcome. When need for guidewire exchange arises while the multi-mode catheter is deployed in rapid-exchange mode (which is equivalent of conventional rapid-exchange catheter deployment), the guidewire 60 is pulled out of the patient while keeping the balloon catheter 10 in place in the patient. Then a new guidewire is reinserted, this time through the proximal opening 44 of the guidewire lumen 20 and is advanced through the entire length of the guidewire lumen 20 and out of the distal opening 46 and into the artery. This guidewire exchange manipulation is similar to the technique discussed on the section (4) earlier.

9) Perfusion Capability of the Multi-Mode Catheter

One of the potential benefits of the multi-mode balloon catheter system of the present invention is its perfusion capability. This capability can be provided both in rapid-exchange mode and in over-the-wire mode, during the periods of balloon inflation.

This capability can be achieved in two different manners. The first approach is to locate the side port 40 close to the balloon segment (e.g., within 5, 10, or 15 cm) The second approach is to provide a second side port 81 (FIG. 4) between the first side port 40 and the balloon. For clinical application, however, either approach would be suitable.

With an additional side port near the proximal end of the balloon, the desired perfusion during balloon inflation can be achieved by simply pulling the guidewire tip back, proximal to the second side port 81 (FIG. 4) but distal to the first side port 40. This will remove all obstructions inside the distal guidewire lumen. The blood may then flow in through the second side port and flow through the distal guidewire lumen 20 and out of the distal catheter tip 46 into the coronary artery. In this design, perfusion could be achieved with equal ease in both rapid-exchange mode and over-the-wire mode.

Although the present invention has been described in the context of certain preferred embodiments, it will be understood that variations to the actual structures illustrated are considered to fall within the scope of the present invention and to be equivalents. For example, the particular configuration of slits and aprons described in connection with FIGS. 2 and 3 may alternatively be replaced with other structure capable of the same function.

Having thus described the invention, the Applicant sets forth the following claims, noting that these claims should not be limited to the specific embodiments described in the detailed description:

What is claimed is:

1. An intravascular catheter, comprising;
   a catheter shaft having a proximal end, a side, and a distal end, wherein a portion of said catheter shaft including said distal end is adapted for insertion into and use within the vasculature of a patient;
   a guidewire lumen extending through said shaft constructed for receiving a steerable guidewire extending the entire length of said guidewire lumen, wherein said guidewire lumen has a proximal opening at the proximal end of said shaft adapted for insertion of a guidewire into said guidewire lumen, a distal opening at the distal end of said shaft, and a side port comprising a permanently formed opening through the side of said catheter shaft into said guidewire lumen which is adapted for passage of a guidewire into said guidewire lumen through the side of said catheter shaft, said side port being located distally of said proximal opening; and
   a guidewire extending through said side port distally into said guidewire lumen and out of said distal opening.

2. The catheter of claim 1, wherein at least a portion of the guidewire lumen proximal of the side port is collapsible when a guidewire is not located in the guidewire lumen.

3. The catheter of claim 2, wherein the outside wall of the guidewire lumen distal to the side port is noncollapsible.

4. The catheter of claim 1, further comprising a guidewire running generally parallel to the axis of said catheter shaft, wherein said guidewire is outside of the guidewire lumen at points proximal to said side port and extends through said side port and is inside said guidewire lumen at points distal to said side port.

5. The catheter of claim 1, wherein the outside wall of the guidewire lumen distal to the side port is noncollapsible.

6. A method of exchanging a catheter while performing a procedure involving vascular catheterization, comprising the steps of:
   positioning a guidewire in the vascular system of a patient;
   providing first and second angioplasty catheters, said catheters each comprising:
   a catheter shaft having a proximal end and a distal end;
   an angioplasty balloon attached to said shaft at said distal end;
   a balloon inflation lumen extending through said shaft and communicating with the interior of said balloon; and
   a guidewire lumen extending through said shaft and through said balloon for receiving a steerable guidewire, wherein said guidewire lumen has a proximal opening at the proximal end of said shaft for insertion of a guidewire into said lumen, and a side port for passage of a guidewire into said lumen through the side of said catheter shaft, said side port located distally of said proximal opening,
   positioning said first catheter on said guidewire so that said guidewire is outside the guidewire lumen proximally of said side port and inside the guidewire lumen distally of said side port;

advancing said first catheter along said guidewire into said vascular system;

removing said first catheter while maintaining said guidewire in said vascular system;

positioning said second catheter on said guidewire with said guidewire inside said guidewire lumen distally of said side port and outside the guidewire lumen proximally of said side port; and advancing said second catheter along said guidewire into said vascular system.

7. A method of exchanging a guidewire during a procedure involving vascular catheterization, comprising the steps of:

positioning a guidewire in the vascular system of a patient;

providing a catheter, said catheter comprising:

a catheter shaft having a proximal end and a distal end;

an angioplasty balloon attached to said shaft at said distal end;

a balloon inflation lumen extending through said shaft and communicating with the interior of said balloon; and a guidewire lumen extending through said shaft and through said balloon for receiving a steerable guidewire, wherein said guidewire lumen has a proximal opening at the proximal end of said shaft for insertion of a guidewire into said lumen, and a side port for passage of a guidewire into said lumen through the side of said catheter shaft, said side port located distally of said proximal opening;

positioning said catheter on said guidewire so that said guidewire passes through said side port and is outside the catheter shaft proximally of said side port and inside the catheter shaft distally of said side port;

advancing the catheter along said guidewire into said vascular system;

removing said guidewire while maintaining said catheter in said vascular system; and inserting a second guidewire into said catheter distally through said proximal opening of said guidewire lumen, through said guidewire lumen past said side port, and out of the distal end of said catheter.

8. A method of exchanging a catheter during a procedure involving vascular catheterization, comprising the steps of:

providing first and second angioplasty catheters, each of said catheters comprising:

a catheter shaft having a proximal end and a distal end;

an angioplasty balloon attached to said shaft at said distal end;

a balloon inflation lumen extending through said shaft and communicating with the interior of said balloon; and a guidewire lumen extending through said shaft and through said balloon for receiving a steerable guidewire, wherein said guidewire lumen has a proximal opening at the proximal end of said shaft for insertion of a guidewire into said lumen, and a side port for passage of a guidewire into said lumen through the side of a said catheter shaft, said side port located distally of said proximal opening, said first catheter having a guidewire passing through said guidewire lumen from the proximal opening to the distal opening thereof and positioning said catheter in a patient;

removing said catheter from said patient while maintaining said guidewire in said patient;

positioning said second catheter on said guidewire so that said guidewire passes through said side port and is inside said guidewire lumen distally of said side port and outside said guidewire lumen proximally of said side port; and advancing said second catheter along said guidewire into said patient while maintaining the positioning of the guidewire.

9. A readily exchangeable dilation catheter which is suitable for performing angioplasty procedures within a patient's vasculature and which permits the exchange of a guidewire during an angioplasty procedure, comprising:

(a) an elongated catheter body having proximal and distal ends, a first lumen adapted to receive a guidewire and extending within said catheter body to the distal end thereof, and a second lumen adapted to direct inflation fluid therethrough and extending within said catheter body to a distal portion thereof;

(b) an inflatable member on a distal portion of said catheter body, said inflatable member having an interior in fluid communication with said second lumen;

(c) a first guidewire port in said catheter body and located at the proximal end of said catheter body, said first guidewire port being in communication with said first lumen;

(d) a second guidewire port in said catheter body being spaced at least 10 cm from said distal end of said catheter body and a substantial distance from the proximal end of said catheter body, and being in communication with said first guidewire-receiving inner lumen;

(e) a third guidewire port in the distal end of said catheter body distal to said inflatable member, said third guidewire port being in communication with said first lumen; and (f) means on the proximal end of said catheter body for directing inflation fluid to the interior of said inflatable member through said second lumen.

10. The intravascular catheter of claim 9, wherein the second guidewire port is spaced no more than 40 cm from the distal end of the catheter body.

11. A method of exchanging a guidewire during an intravascular procedure within a patient's vascular system, comprising:

(a) providing an intravascular catheter which includes:

(i) an elongated catheter body having proximal and distal ends, a guidewire-receiving inner lumen extending within said catheter body to the distal end thereof;

(ii) diagnostic or therapeutic means on the distal portion of said catheter body;

(iii) a first guidewire port in said catheter body at the proximal end of said catheter body and in communication with said guidewire-receiving inner lumen;

(iv) a second guidewire port in said catheter body being spaced proximally from said diagnostic and therapeutic means at least 10 cm from the distal end of said catheter body and being in communication with said guidewire-receiving inner lumen; and (v) a third guidewire port in the distal end of said catheter body and which is in communication with said guidewire-receiving inner lumen;

(b) disposing said intravascular catheter within the vascular system of the patient with an in-place guidewire disposed within said guidewire-receiving inner lumen with the distal end thereof extending out said third guidewire port into the patient's vascular system and the proximal end extending out said second guidewire port;

(c) withdrawing said in-place guidewire from the patient's vascular system by pulling on the proximal end thereof while holding the intravascular catheter in place, so as to maintain access to the location of said in-place guidewire within the patient's vascular system; and (d) advancing within said guidewire-receiving inner lumen of the intravascular catheter a replacement guidewire, which is disposed within said guidewire-receiving inner lumen with the proximal end of said replacement guidewire extending proximally out of said first guidewire port and distally out of said third guidewire port into the patient's vascular system, until the distal end of said replacement guidewire extends beyond the location of the intravascular procedure.

12. The method of claim 11, wherein said diagnostic or therapeutic means is an inflatable balloon suitable for angioplasty procedures.

13. The method of claim 12, wherein said intravascular catheter has an inner lumen extending within said catheter body for directing inflation fluid from the proximal end of said catheter body to the interior of said inflatable balloon.

14. A method of exchanging a guidewire during a procedure involving vascular catheterization comprising the steps of:

providing a guidewire in the vascular system of a patient;

providing an intravascular catheter, comprising:

a catheter shaft having a proximal end and a distal end, wherein a portion of said distal end is inside a patient during use;

a guidewire lumen extending through said shaft for receiving a steerable guidewire, wherein said guidewire lumen has a proximal opening at the proximal end of said shaft for insertion of a guidewire into said lumen, and a side port for passage of a guidewire into said lumen through the side of said catheter shaft, said side port located distally of said proximal opening, positioning said catheter on said guidewire so that said guidewire passes through said side port and is outside the catheter shaft proximally of said side port and inside the catheter shaft distally of said side port;

advancing said catheter along said guidewire into said vascular system;

removing said guidewire while maintaining said catheter in said vascular system; and inserting a second guidewire into said catheter distally through said proximal opening of said guidewire lumen, through said guidewire lumen past said side port, and out of the distal end of said catheter.

* * * * *